United States Patent [19]
Frey et al.

[11] Patent Number: 5,849,006
[45] Date of Patent: Dec. 15, 1998

[54] LASER SCULPTING METHOD AND SYSTEM

[75] Inventors: Rudolph W. Frey; James H. Burkhalter; Gary P. Gray, all of Orlando, Fla.

[73] Assignee: Autonomous Technologies Corporation, Orlando, Fla.

[21] Appl. No.: 232,956

[22] Filed: Apr. 25, 1994

[51] Int. Cl.$^6$ .................................................. A61N 5/06
[52] U.S. Cl. ...................................... 606/5; 606/4
[58] Field of Search ............................... 128/745; 606/4, 606/5, 6, 10, 11, 12

[56] References Cited

U.S. PATENT DOCUMENTS

| | | |
|---|---|---|
| 4,669,466 | 6/1987 | L'Esperance . |
| 4,729,372 | 3/1988 | L'Esperance, Jr. .......................... 606/4 |
| 4,941,093 | 7/1990 | Marshall et al. ............................. 606/4 |

FOREIGN PATENT DOCUMENTS

| | | |
|---|---|---|
| 0 151 869 | 8/1985 | European Pat. Off. . |
| 8706478 | 11/1987 | WIPO ...................................... 606/10 |

Primary Examiner—Robert L. Nasser
Attorney, Agent, or Firm—Allen, Dyer, Doppelt, Milbrath & Gilchrist, P.A.

[57] ABSTRACT

A method and system are provided for eroding or ablating a shaped volume of an eye's corneal tissue in accordance with the treatment of a specified eye condition. To determine the laser beam shot pattern, a plurality of laser beam shots of uniform intensity are first selected to form a uniform shot pattern of uniform shot density. The laser beam shots applied in accordance with the uniform shot pattern of uniform shot density would be capable of eroding a volume of the corneal tissue of uniform height. The volume of uniform height is approximately equivalent to that of the shaped volume. The laser beam shots are applied to the corneal tissue in a spatially distributed pattern spread over an area approximately equivalent to the surface area of the shaped volume to be eroded. The spatially distributed pattern extends the uniform shot pattern in fixed angles from a reference position on the shaped volume representative of the shaped volume's axis of symmetry. Shot density for the laser beam shots changes in correspondence with distance from the reference position.

11 Claims, 6 Drawing Sheets

LASER SCULPTING METHOD AND SYSTEM

FIELD OF THE INVENTION

The invention relates generally to ophthalmic laser surgery, and more particularly to a method and system for arranging a pattern of laser shots to erode a shaped volume of corneal tissue in accordance with the treatment of a specified eye condition.

BACKGROUND OF THE INVENTION

Photorefractive keratectomy (PRK) is a procedure for laser correction of focusing deficiencies of the eye by modification of corneal curvature. PRK is distinct from the use of laser-based devices for more traditional ophthalmic surgical purposes, such as tissue cutting or thermal coagulation. PRK is generally accomplished by use of a 193 nanometer wavelength excimer laser beam that ablates away corneal tissue in a photo decomposition process. Most clinical work to this point has been done with a laser operating at a fluence level of 120–195 $mJ/cm^2$ and a pulse-repetition rate of approximately 5–10 Hz. The procedure has been referred to as "corneal sculpting."

Before sculpting of the cornea takes place, the epithelium or outer layer of the cornea is mechanically removed to expose Bowman's membrane on the anterior surface of the stroma. At this point, laser ablation at Bowman's layer can begin. An excimer laser beam is preferred for this procedure. The beam may be variably masked during the ablation to remove corneal tissue to varying depths as necessary for recontouring the anterior stroma. Afterward, the epithelium rapidly regrows and resurfaces the contoured area, resulting in an optically correct (or much more nearly so) cornea.

For ablation to occur, the energy density of the laser beam must be above some threshold value, which is currently accepted as being approximately 60 $mJ/cm^2$. Such energy densities can be produced by a wide variety of commercially available lasers. For example, a laser could be used that is capable of generating a laser beam of diameter large enough to cover the surface to be ablated, i.e., on the order of 4.5–7.0 millimeters in diameter. However, such laser beams are typically not regular in intensity thereby causing a rough surface ablation. Further, lasers capable of producing such laser beams are typically, large, expensive and prone to failure.

Alternatively, a laser could be used that produces a much smaller diameter laser beam, i.e., on the order of 0.5–1.0 millimeters in diameter. There are several advantages afforded by the smaller diameter laser beam. They can be generated to meet the above noted threshold requirement with a lower energy pulse than that of the larger diameter beam. Further, such smaller diameter laser beams can be produced with a regular intensity while minimizing the variance in pulse-to-pulse energy levels. Finally, lasers producing the smaller diameter laser beam are physically smaller, less expensive and, frequently, more reliable. However, this requires that the position of the small pulses be precisely controlled so that the resulting ablated surface is smoother than that which is produced by the larger laser beam.

SUMMARY OF THE INVENTION

Accordingly, it is an object of the present invention to provide a method and system of laser sculpting suitable for the recontouring of corneal tissue.

Another object of the present invention is to provide a method and system for arranging a pattern of small diameter, regular intensity laser pulses or shots to erode or ablate a shaped volume of corneal tissue in accordance with the treatment of a specific eye condition.

Still another object of the present invention is to provide a method and system of laser sculpting that is designed to use small inexpensive lasers.

Other objects and advantages of the present invention will become more obvious hereinafter in the specification and drawings.

In accordance with the present invention, a method and system are provided for eroding or ablating a shaped volume of an eye's corneal tissue in accordance with the treatment of a specified eye condition. A plurality of laser beam shots of uniform intensity are selected to form a uniform shot pattern of uniform shot density. If the laser beam shots were applied in accordance with the uniform shot pattern of uniform shot density, they would be capable of eroding a volume of the corneal tissue of uniform height. The volume of uniform height is approximately equivalent to that of the shaped volume. The laser beam shots are actually applied to the corneal tissue in a spatially distributed pattern spread over an area approximately equivalent to the surface area of the shaped volume to be eroded. The spatially distributed pattern is obtained by distorting the uniform shot pattern in a fixed manner from a reference position on the shaped volume representative of the shaped volume's axis of symmetry. Shot density for the laser beam shots changes in correspondence with distance from the reference position. The particular spatial distribution and change in shot density is adjusted to treat the eye conditions of myopia, hyperopia and astigmatism.

This patent application is copending with related patent applications entitled "Laser Beam Delivery and Eye Tracking System" filed on the same date and owned by a common assignee as subject patent application. The disclosures of these two applications are incorporated herein by reference.

DETAILED DESCRIPTION OF THE INVENTION

Figure 1A:
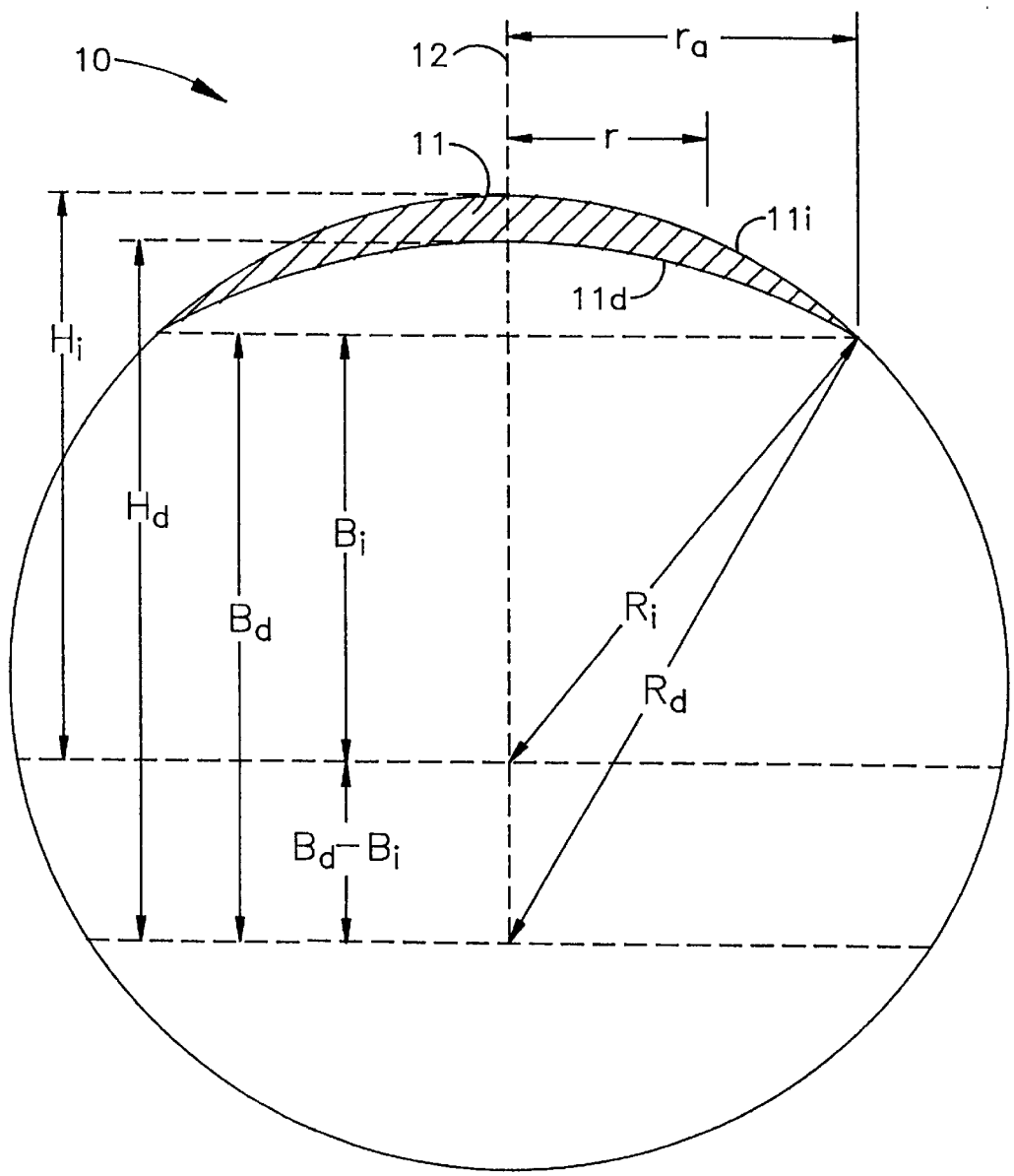
FIG. 1A is a diagrammatic view of an eye showing a meniscus shape of corneal tissue associated with the condition of myopia that is to be ablated volumetrically in accordance with the present invention.

Referring now to the drawings, and more particularly to FIG. 1A, a diagrammatic view is shown of an eye designated generally by reference numeral 10. Eye 10 has a meniscus of surface material, i.e., corneal tissue, as indicated by hatched area 11, that is to be eroded by a small diameter laser beam (e.g., on the order of 0.5–1.0 millimeters in diameter) in accordance with the present invention. By way of example, meniscus 11 represents a shaped volume of corneal tissue, symmetrical about visual axis 12, that is to be eroded to correct the condition of myopia. Accordingly, the thickness T(r) of meniscus 11 is maximum at visual axis 12, i.e., r=0, of eye 10 and decreases to zero at the outside edge, i.e., r=$r_A$, of meniscus 11. However, it is to be understood that the method and system of the present invention are applicable for other eye conditions such as hyperopia and astigmatism as will be explained further below.

As is known in the art, either direct or indirect measurements can be made to determine the radius curvature $R_i$ of outside surface $11_i$ of meniscus 11 (i.e., the corneal surface of eye 10 prior to laser treatment). The radius of curvature $R_D$ of inside surface $11_D$ of meniscus 11 (i.e., the corneal surface of eye 10 after laser treatment) is known based on the desired refractive correction. The radius of aperture $r_A$ of meniscus 11 (i.e., the treatment or optical zone) is defined by the doctor. Given these values, it is possible to determine the volume of meniscus 11 as follows for any radius of aperture r, $0 \leq r \leq r_A$.

Figure 1B:
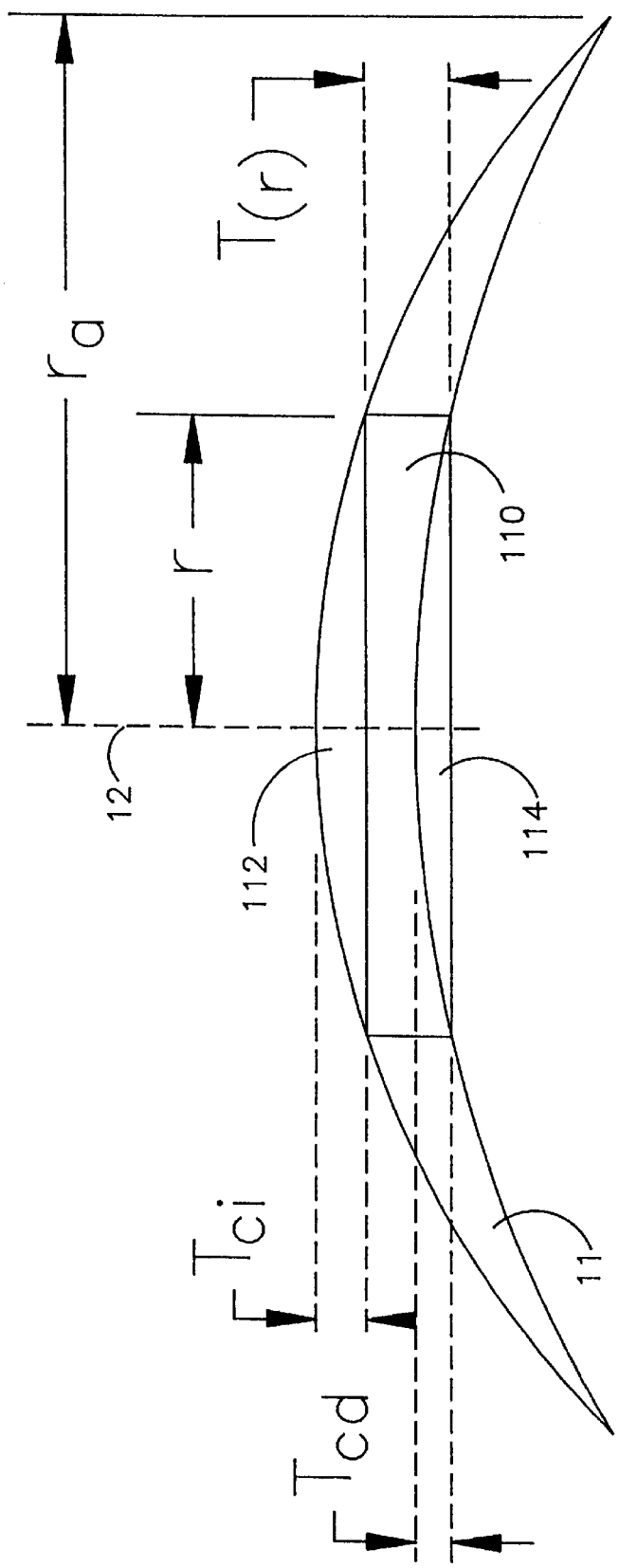
FIG. 1B is an enlarged isolated view of the meniscus of FIG. 1A.

The meniscus volume out to a radius r is the algebraic sum of the volume of cylinder 110 of radius r and thickness T(r), plus the volume of spherical cap 112 of center thickness $t_{ci}$, minus the volume of spherical cap 114 of center thickness $t_{cD}$ (which is included in cylinder 110). This is best seen in FIG. 1B where meniscus 11 is enlarged and shown in isolation. The volumes $V_{ci}$ and $V_{cD}$ of caps 112 and 114, respectively, are $$v_{ci} = \pi * t_{ci}^2 * \left( R_i - \frac{t_{ci}}{3} \right) \tag{1}$$

and $$v_{cD} = \pi * t_{cD}^2 * \left( R_D - \frac{t_{cD}}{3} \right) \tag{2}$$

and the thickness T(r) of cylinder 110 is $$T(r) = (h_i - B_i) - (h_D - B_D) \tag{3}$$

where $$h_i = \sqrt{(R_i^2 - r^2)} \tag{4}$$

$$h_D = \sqrt{(R_D^2 - r^2)} \tag{5}$$

$$B_i = \sqrt{(R_i^2 - r_A^2)} \tag{6}$$

and $$B_D = \sqrt{(R_D^2 - r_A^2)} \tag{7}$$

Substituting equations (4)–(7) into equation (3), T(r) becomes a function of r, $r_A$, $R_i$, and $R_D$. The volume $V_{cl}$ of cylinder 110 is thus $$V_{cl} = \pi * r^2 * T(r, r_A, R_i, R_D) \tag{8}$$

and the volume of meniscus 11 at a radius r is $$V_r = V_{cl} + V_{ci} - V_{cD}. \tag{9}$$

Since the volume of material ablated by each laser beam shots is known in advance, the number of laser beam shots N required to ablate meniscus 11 is easily calculated using the volume of meniscus 11. Further, the local shot density at visual axis 12, where r=0 to yield thickness T(0), is easily calculated.

Figure 2:
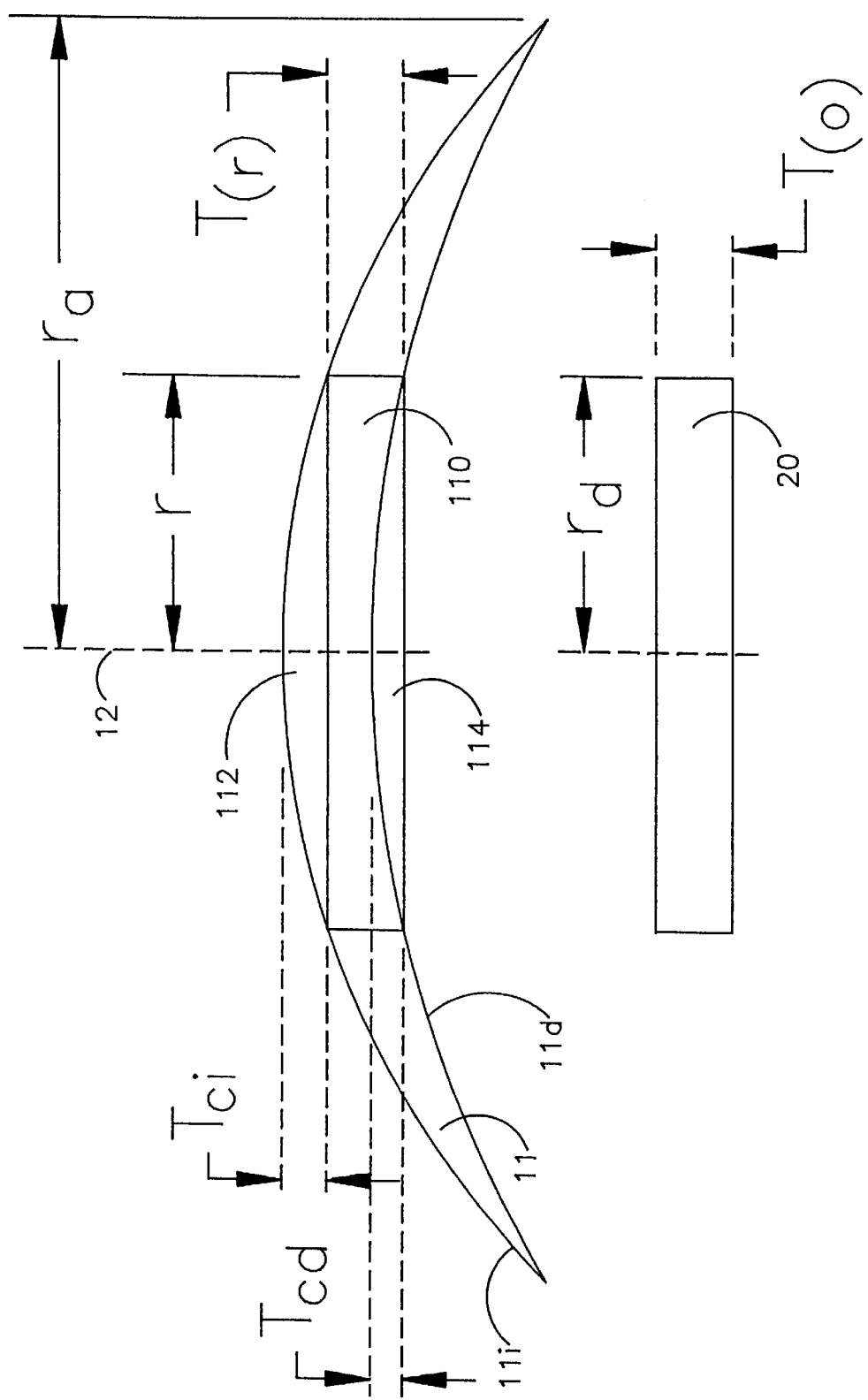
FIG. 2 is an isolated view of the meniscus of FIG. 1A shown in comparison to a cross-section of a uniform cylinder dimensioned to have the same volume as that of the meniscus in accordance with the operation of the present invention.

The method of the present invention begins by selecting a uniform pattern such that if the N laser beam shots were applied with a uniform shot density over the uniform pattern, a cylinder of height T(0) would be ablated. The volume of such a cylinder would be equal to the volume of meniscus 11 and its radius would be $r_D$ where $r_D < r_A$. This is depicted in FIG. 2 where a cross-section of cylinder 20 of radius $r_D$ and height T(0) is shown in comparison to meniscus 11.

To achieve the desired ablation of meniscus 11, the N laser beam shots must be spatially distributed to obtain smooth transitions between the resulting surface ablations. Conceptually, the present invention first fixes the local area density of laser beam shots at the axis of symmetry of meniscus 11, i.e., visual axis 12, to be equal to that of the uniform shot density represented by cylinder 20. The shot density represented by cylinder 20 is then stretched or extended radially from visual axis 12 over the surface area formed by surface $11_i$ out to $r_A$ while steadily decreasing the laser beam shot density. The angles between each shot position in the uniform pattern of cylinder 20 and the actual pattern incident on eye 10 remain the same. In other words, the extension of shot positions occurs only in the radial direction.

The thickness of meniscus 11 at any radius r or T(r) is proportional to its local area density of laser beam shots. The center value of T(r) at r=0 is equal to the height of cylinder 20. As the positions of the shot pattern on cylinder 20 are extended radially, the center height or shot density remains unchanged and the local area density at other points must be determined. The relationship between any radius r of meniscus 11 and $r_D$ is $$\int_r^0 V(u) du = T(0) * \pi * r_D^2 \tag{10}$$

where du is the differential volume of the meniscus as a function of r which is the integration variable. This relationship may be digitized for ease of processing as follows.

Take a series of values $r_j$, j=1, 2, ... $j_{max}$ where $r_{j\,max} = r_A$, and $dr = (r_{j+1} - r_j)$. Further, let the corresponding values of $r_D$ be called $r_{Dj}$. Then $$\sum_0^{(j-1)} V(r_k) dr = T(0) * \pi * r_{Dj}^2 = \pi * T(0) * \sum_0^{(j-1)} r_{Dk}^2 \tag{11}$$

If r is extended over n equal steps, where n is selected to be as large as possible to minimize error, then $dr = r_A/n$ and $r_j = j*dr$. Then, $$\pi *T(0)*i\; r_{Dk}^2 = V(k*dr) = V(k*r_A/n) \tag{12}$$

where k=0, 1, 2, . . . , n.

Since the volume meniscus 11 at any radius r can be determined using equation (9), equation (12) can be solved for $r_{Dk}$ and the radius of cylinder 20 is extended to $r_k$. Thus, the ratio $r_K/r_{Dk}$ is the desired stretch factor. The effect of the "stretch" is to decrease the density of the laser beam shots as the radial distance from the center of the eye increases. The gradually changing laser beam shot density, combined with a small ablation volume brought about by the use of a small diameter laser, provides for smooth transition from the thick portion of meniscus 11 to the thin portion of meniscus 11. At a wavelength of 193 nanometers and a fluence of 160 mJ/cm$^2$, each pulse ablates the corneal surface to a depth of about 0.25 $\mu$m. By distributing laser shot density in accordance with the above described procedure, the resulting ablated corneal surface is very smooth.

Figure 3:
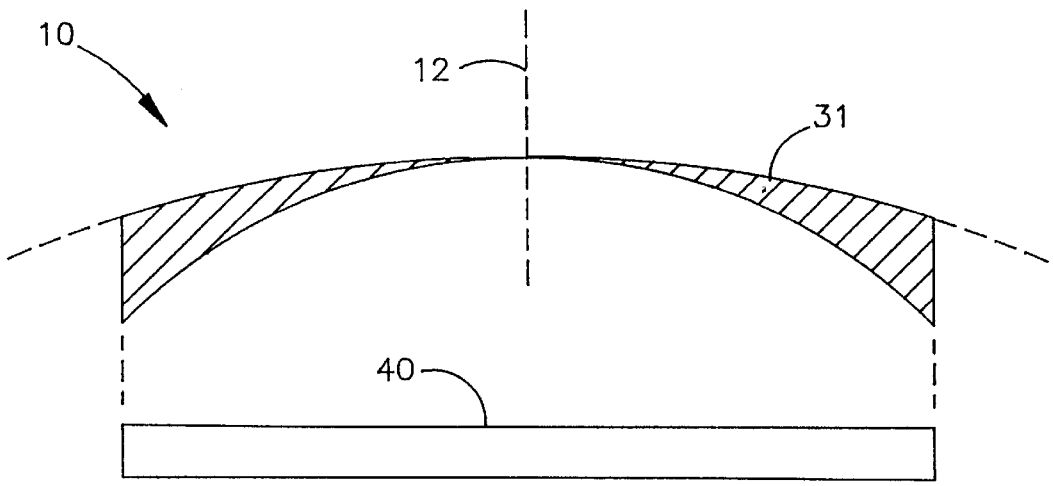
FIG. 3 is a diagrammatic view of an eye showing a shape of corneal tissue associated with the condition of hyperopia that is to be ablated volumetrically in accordance with the present invention along with a cross-section of a uniform cylinder dimensioned to have the same volume as that of the volume represented by the shape.

For the eye condition known as hyperopia, the present invention determines and applies the required laser beam shot pattern in a fashion very similar to that just described for the case of myopia. In the case of hyperopia, the surface of the eye's cornea is too flat and needs to be made steeper, i.e., the corneal radius of curvature must be decreased. Referring to FIG. 3, a diagrammatic view is shown of hatched shape 31 which is representative of a volumetrically symmetric shape about visual axis 12. The volume represented by shape 31 must be ablated from eye 10 (which has been shown in dotted line form in order to highlight shape 31) in order to correct the condition of hyperopia. The total volume of shape 31 and number of laser beam shots N required to ablate same is first determined. Then, a uniform shot pattern of uniform shot density is selected such that cylinder 40 (shown in cross-section) of uniform height and a radius equal to that of shape 31 would be formed if the uniform shot pattern were applied to corneal tissue.

To achieve the desired ablation of shape 31, the N laser beam shots must be spatially distributed to obtain smooth transitions between the resulting surface ablations. Conceptually, this is achieved by redistributing the uniform shot density represented by cylinder 40. The local area density of laser beam shots at the axis of symmetry, i.e., visual axis 12, is decreased to zero while shot density is steadily increased in a fixed angle radial fashion out to the perimeter of shape 31. Thus, the final shot density profile will closely approximate that of shape 31 which is to be ablated. Depending on the amount of correction required, it may also be necessary to apply additional laser beam shots to eye 10 just beyond the treatment zone represented by shape 31 in order to provide a smooth transition between the treated and untreated portions of eye 10.

Figure 4:
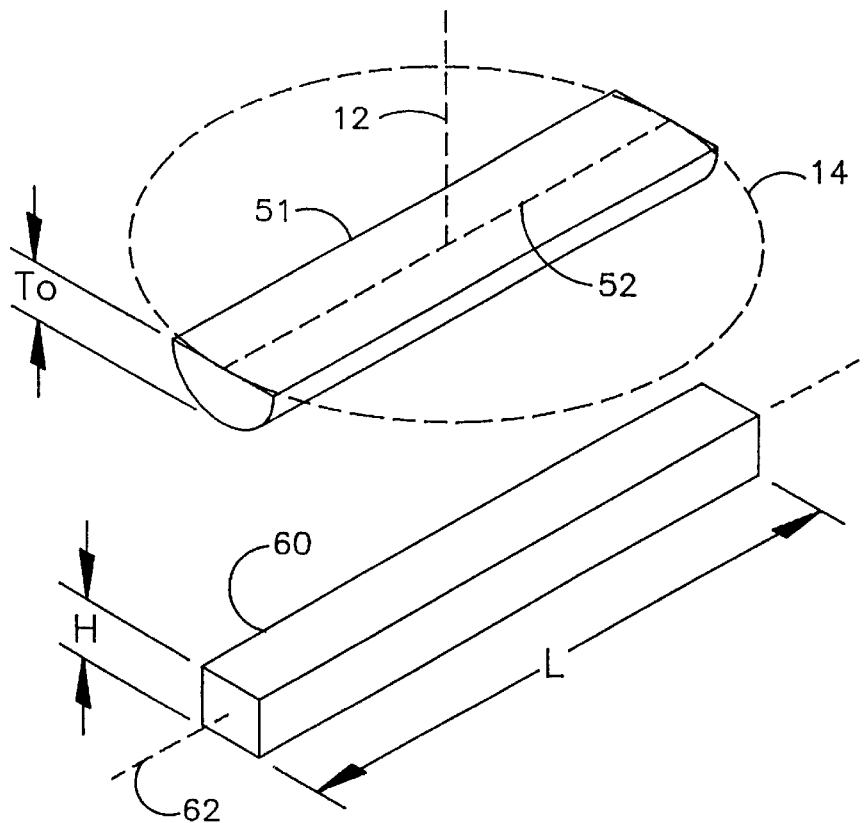
FIG. 4 is a diagrammatic perspective view of the treatment zone of an eye showing a shape of corneal tissue associated with the condition of astigmatism that is to be ablated volumetrically in accordance with the present invention along with a uniform rectangular prism dimensioned to have the same volume as that of the volume represented by the shape.

Both the myopia and hyperopia conditions require that a volume of corneal tissue be removed which is radially symmetric about the eye's visual axis. However, the condition known as astigmatism is different in that it has an axis of symmetry in the plane perpendicular to the eye's visual axis. Further, the correction for astigmatism assumes that the surface of the eye is flat. This is shown diagrammatically in the perspective view of FIG. 4 where the flat surface of the eye that is to be treated, i.e., the treatment zone, is represented by dotted line 14. The correction requires that portion 51 of a cylinder be removed from the cornea. Portion 51 has a thickness that is $T_0$ along its central axis 52 and decreasing out to its perimeter. Once again, the volume of corneal tissue to be removed and number of laser beam shots N required to do so is first determined. Then, a uniform shot pattern of uniform shot density is selected such that rectangular prism 60 having central longitudinal axis 62 would be generated by the N laser beam shots. Rectangular prism 60 has a uniform height H that is equivalent to the thickness $T_0$ along the central axis of portion 51. The length L of rectangular prism 60 should be sufficient to span the diameter of treatment zone 14.

To achieve the desired ablation of portion 51, the N laser beam shots must be spatially distributed to obtain smooth transitions between the resulting surface ablations. Conceptually, this is achieved by redistributing the uniform shot density represented by rectangular prism 60. The local area density of laser beam shots at the axis of symmetry, i.e., central axis 52 of portion 51, is set to be equal to the uniform shot density of rectangular prism 60. Shot density is then gradually decreased to zero as the uniform shot pattern represented by rectangular prism 60 is stretched outward in opposite directions from center axis 62 in the plane perpendicular to visual axis 12. Thus, the final shot density profile will closely approximate that of portion 51 which is to be ablated. Note that not all of the N laser beam shots are applied. In particular, the laser beam shots associated with portion 51 lying outside of treatment zone 14 are truncated.

The present invention may be further extended to the case of irregular astigmatism which is described by a generalized corneal shape having no overall axis of symmetry. In this case, the overall volume to be eroded may be approximated by a multiplicity of locally symmetric volumes that are summed together. Each of the symmetric volumes is selected so that ablation thereof may be carried out in accordance with one of the above described methods.

Figure 5:
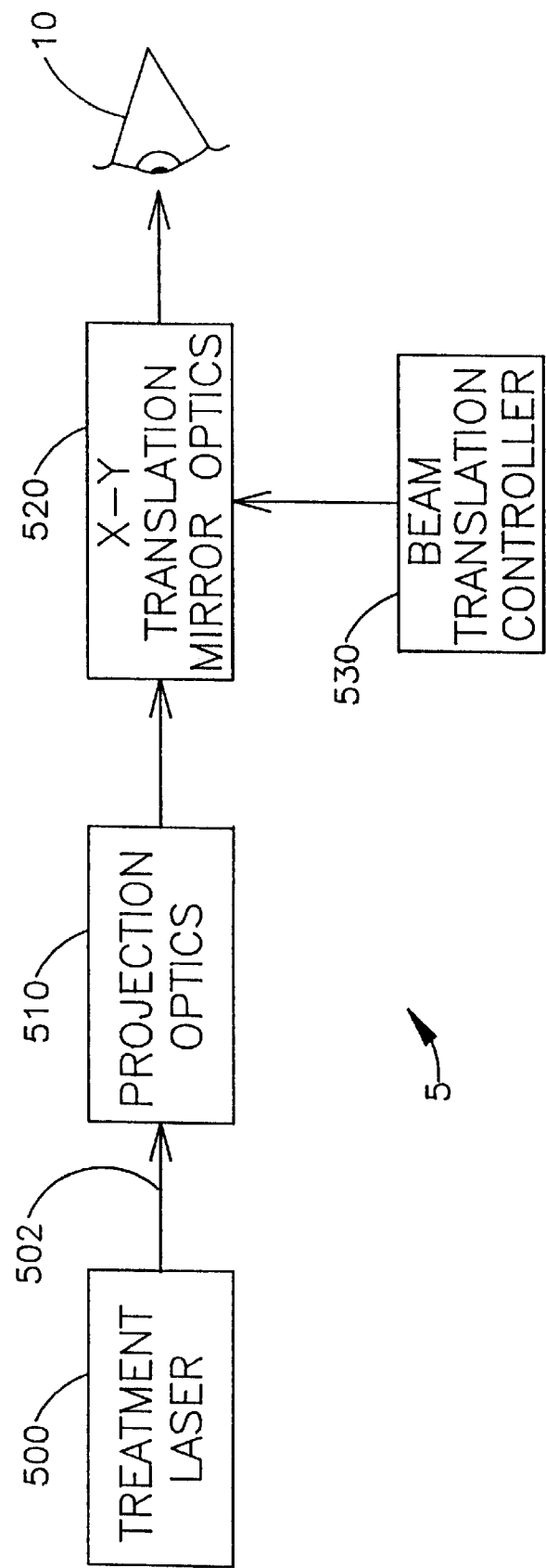
FIG. 5 is a block diagram of the laser sculpting system in accordance with the present invention.

To implement the above described procedures, a system 5 is shown in FIG. 5 in block diagram form. System 5 includes treatment laser 500 producing laser beam 502, projection optics 510, X-Y translation mirror optics 520 and beam translation controller 530. Treatment laser 500 is typically a pulsed output laser. By way of example, it will be assumed that treatment laser 500 is a 193 nanometer wavelength pulsed excimer laser used in an ophthalmic PRK procedure performed on eye 10. However, it is to be understood that the method and system of the present invention will apply equally as well to workpieces other than an eye, and further to other wavelength surface treatment or surface eroding lasers where it is desirable to erode a shaped volume of surface material.

Figure 6:
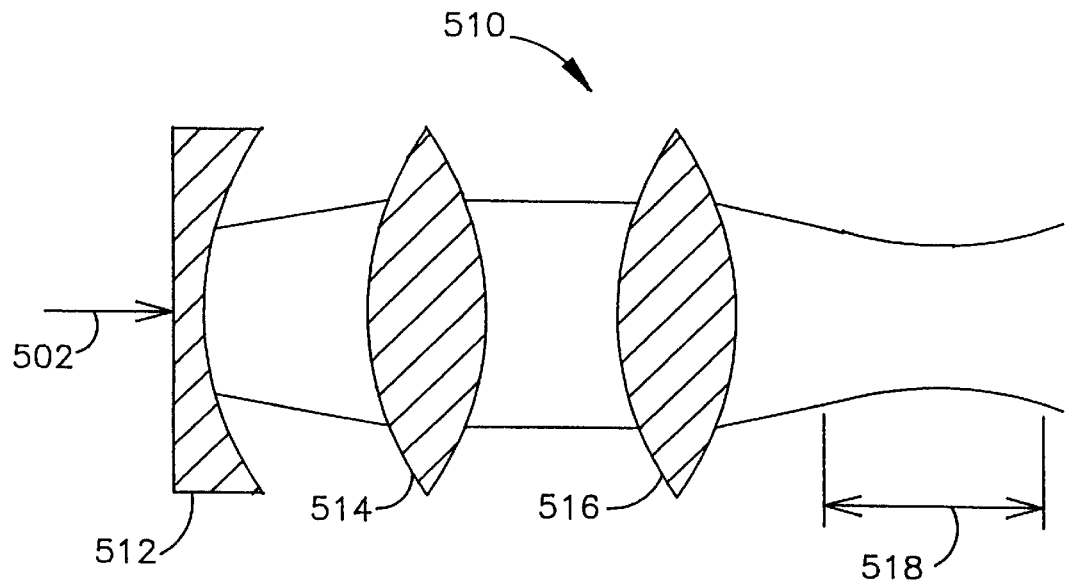
FIG. 6 depicts diagrammatically an arrangement for the projection optics of the present invention.

Laser beam 502 is incident upon projection optics 510. Projection optics 510 adjusts the diameter and distance-to-focus of beam 502 depending on the requirements of the particular procedure being performed. For the illustrative example of an excimer laser used in the PRK procedure, projection optics 510 includes planar concave lens 512, and fixed focus lenses 514 and 516 as shown in the diagrammatic arrangement of FIG. 6. Lenses 512 and 514 act together to form an A-focal telescope that expands the diameter of beam 502. Fixed focus lens 516 focuses the expanded beam 502 at the workpiece, i.e., eye 10, and provides sufficient depth, indicated by arrow 518, in the plane of focus of lens 516. This provides flexibility in the placement of projection optics 510 relative to the surface of the workpiece. An alternative implementation is to eliminate lens 514 when less flexibility can be tolerated.

After exiting projection optics 510, beam 502 impinges on X-Y translation mirror optics 520 where beam 502 is translated or shifted independently along each of two orthogonal translation axes as governed by beam translation controller 530. Controller 530 is typically a processor programmed with a predetermined set of two-dimensional translations or shifts of beam 502 depending on the particular ophthalmic procedure being performed. Thus, controller 530 is programmed in accordance with one of the above described shot pattern distribution methods depending on the eye condition being treated. The programmed shifts of beam 502 are implemented by X-Y translation mirror optics 520.

Figure 7:
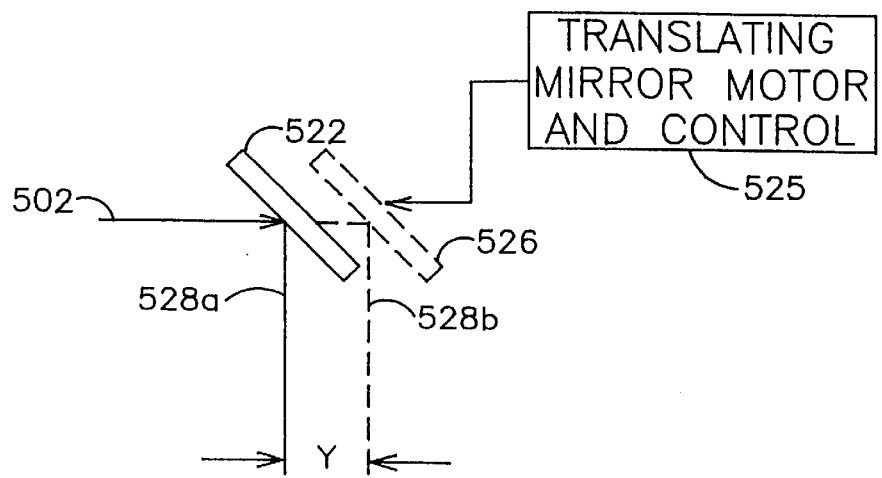
FIG. 7 illustrates diagrammatically an optical arrangement of mirrors used to produce translational shifts in a light beam along one axis of translation.

Each X and Y axis of translation is independently controlled by a translating mirror. As shown diagrammatically in FIG. 7, the Y-translation operation of X-Y translation mirror optics 520 is implemented using translating mirror 522. Translating mirror 522 is movable between the position shown and the position indicated by dotted line 526. Movement of translating mirror 522 is such that the angle of the output beam with respect to the input beam remains constant. Such movement is brought about by translating mirror motor and control 525 driven by inputs received from beam translation controller 530. By way of example, motor and control 525 can be realized with a motor from Trilogy Systems Corporation (e.g., model T050) and a control board from Delta Tau Systems (e.g., model 400-602276 PMAC).

With translating mirror 522 positioned as shown, beam 502 travels the path traced by solid line 528a. With translating mirror 522 positioned along dotted line 526, beam 502 travels the path traced by dotted line 528b. A similar translating mirror (not shown) would be used for the X-translation operation. The X-translation operation is accomplished in the same fashion but is orthogonal to the Y-translation. The X-translation may be implemented prior or subsequent to the Y-translation operation.

Although the invention has been described relative to a specific embodiment thereof, there are numerous variations and modifications that will be readily apparent to those skilled in the art in the light of the above teachings. It is therefore to be understood that, within the scope of the appended claims, the invention may be practiced other than as specifically described.

What is claimed as new and desired to be secured by Letters Patent of the United States is:

1. A method of correcting vision by eroding an eye's corneal tissue comprising the steps of:
   providing for a plurality of laser beam shots of uniform intensity and size;
   determining the volume and shape of corneal tissue to be eroded;
   providing the uniform volume of corneal tissue eroded by each laser beam shot;
   determining the number of laser beam shots needed to erode said volume of corneal tissue to be eroded;
   determining a uniform shot pattern for said number of laser beam shots wherein said uniform shot pattern of laser beam shots is capable of eroding said volume of corneal tissue to be eroded;
   extending said uniform shot pattern to an area approximately equivalent to the surface area of said corneal tissue to be eroded; and
   applying said number of laser beam shots to said corneal tissue in accordance with said extended shot pattern wherein said corneal tissue is eroded to achieve removal of said volume and shape.

2. A method according to claim 1, wherein said vision being corrected is myopia and said step of applying including the step of:
   applying said laser beam shots to said corneal tissue in said extended shot pattern wherein said extended shot pattern extends radially in all directions from the center of said shape and wherein shot density for said laser beam shots decreases in correspondence with radial distance from said center.

3. A method according to claim 1, wherein said vision being corrected is hyperopia and said step of applying including the step of:
   applying said laser beam shots to said corneal tissue in said extended shot pattern wherein said extended shot pattern extends radially in all directions from the center of said shape and wherein shot density increases in correspondence with radial distance from said center.

4. A method according to claim 1, wherein said vision being corrected is astigmatism and said step of applying including the step of:
   applying said laser beam shots to said corneal tissue in said extended shot pattern wherein said extended shot pattern extends from a line in a plane perpendicular to the visual axis in opposite directions wherein shot density for said laser beam shots decreases in correspondence with distance form said line.

5. A method according to claim 1 wherein each of said plurality of laser beam shots has an energy density of at least approximately 60 mJ/cm$^2$.

6. A method according to claim 1 wherein each of said plurality of laser beam shots has a wavelength of approximately 193 nanometers.

7. A method according to claim 1 wherein said uniform shot pattern is hexagonal.

8. A method according to claim 1 wherein said uniform shot pattern is rectangular.

9. A system for eroding an eye's corneal tissue to correct vision, comprising;
   a pulsed laser for producing a plurality of laser beam shots of uniform intensity and size, each of said plurality of laser beam shots traveling on an original beam path;
   a mechanism for shifting said original beam path onto a different beam path in accordance with a predetermined shot pattern, wherein said plurality of said laser beam shots are directed to said corneal tissue to be eroded; and
   a controller for issuing shift control commands to said mechanism in accordance with said predetermined shot pattern, said predetermined shot pattern being based on a uniform shot pattern of uniform shot density for said plurality of laser beam shots, wherein said uniform shot pattern of uniform shot density is capable of eroding a volume of said corneal tissue, said volume being approximately equivalent to that of the volume of a desired shape to be eroded, said mechanism issuing shift control commands to apply said plurality of laser beam shots to said corneal tissue in a pattern spread over an area approximately equivalent to the surface area of said volume to be eroded, said pattern being created by extending said uniform shot pattern from a position on said volume wherein shot density for said of laser beam shots changes in correspondence with distance from said position.

10. A system as in claim 9 wherein said pulsed laser comprises a 193 nanometer wavelength excimer laser producing said laser beam shots of uniform intensity.

11. A system as in claim 9 further comprising projection optics for increasing depth of focus for each of said laser beam shots.

* * * * *